United States Patent [19]

Bretz et al.

[11] Patent Number: 5,500,017
[45] Date of Patent: Mar. 19, 1996

[54] BREAST IMPLANT DEVICE

[76] Inventors: Phillip D. Bretz, 48551 Olympic Dr.; Vincent R. Forshan, 74200 Covered Wagon Trail, both of Palm Desert, Calif. 92260

[21] Appl. No.: 342,054

[22] Filed: Nov. 17, 1994

[51] Int. Cl.$^6$ .................. A61F 2/12; A61F 2/02
[52] U.S. Cl. .................. 623/8; 623/11
[58] Field of Search .................. 623/7, 8, 11, 17

[56] References Cited

U.S. PATENT DOCUMENTS 4,157,085   6/1979   Austad .................. 623/8

*Primary Examiner*—Debra S. Brittingham
*Attorney, Agent, or Firm*—Dennison, Meserole, Pollack & Scheiner

[57] ABSTRACT

A breast implant device formed from a polymeric sac filled with a filling material which is a substantially silicone-free aqueous sugar solution having a viscosity of at least 15 cp at 98.6° F. The filling material is preferably honey.

7 Claims, No Drawings

BREAST IMPLANT DEVICE

BACKGROUND OF THE INVENTION

The invention relates to the field of breast implants, and in particular, filler materials for breast implants.

For well over thirty years, women have been undergoing breast augmentation in the United States. Early efforts included free silicone injections. Over the years, free silicone has coalesced into hard nodular breast masses indistinguishable from cancer, and making mammography all but impossible to read. This in turn has led to aggressive surgery such as subcutaneous mastectomy with often less than desirable results.

Later, implants made of liquid silicone contained within a polymer, typically silicone, sac were used. While the silicone of the sac itself was not generally thought to cause a problem, the tendency of the sacs to rupture or leak over long periods of time created disastrous problems for many users.

The presence of free liquid silicone, whether by injection or by rupture of a silicone implant has had serious local and systemic side effects, particularly migration of the free silicone and collection of silicone in major body organs, such as the liver. The presence of free silicone has incited autoimmune responses in many patients causing a severely debilitated state. Even more serious, in some patients the silicone has been found to cause autoimmune responses even when confined to the polymer sac. One study has shown that some women with breast implants produce antibodies against their own collagen, but it is not known whether this might increase their risk of actually developing an autoimmune-like disorder.

A double lumen silicone/saline implant, with an inner silicone filled sac and an outer saline filled sac, was originally thought to be the answer to the problems with the silicone implant, but has proven to have nearly as many faults. For example, the internal silicone sac can rupture leaving the patient in a state of fear and the physician in a state of indecision as how best to handle the situation. If the double lumen implant, now a single lumen implant, is left in place, the problem of autoimmune disorder becomes potentially more likely with transmigration of minute amounts of silicone out of the intact polymer sac.

The problem of side effects caused by silicone can be eliminated by filling the polymer sac with physiological saline solution. While the saline implant has generally eliminated immune system problems, saline filled sacs have been subject to partial deflation. The package insert of the McGhan Biocell® RTV sac warns that capsular contracture may result in firmness, discomfort or pain in the breast, and/or displacement of the implant. Several published studies have observed a very high incidence of deflation, specifically McGrath et al, "The Safety and Efficacy of Breast Implants for Augmentation Mammaplasty," Plastic & Reconstructive Surgery 74:550 (1984); Williams, "Experience with a Large Series of Silastic Breast Implants," Plastic & Reconstructive Surgery 49:253 (1972); and Grossman, "The Current Status of Augmentation Mammaplasty," Plastic & Reconstructive Surgery 52:1 (1973), the reported incidence of deflation reaching as high as 76%.

The long term cosmetic effects of the saline implant have thus been generally unsatisfactory, the partially deflated sac crinkling, with a wave like effect being felt instead of a full soft breast. The reason for this deflation is speculated as being osmotic pressure, aggravated by a tendency on the part of implanting surgeons to overinflate the sac with saline.

U.S. Pat. No. 4,995,882 has proposed the use of a triglyceride such as peanut oil or sunflower seed oil as a filling for a breast implant, these filling materials having the same average radiographic density as human breast tissue. However, it is known that silicone sac itself interferes with mammography, so utilizing a less interfering filling does not completely solve the mammography problem.

The use of silicone filled implants has now been discontinued in the United States in all cases except for breast reconstruction necessitated by mastectomy for cancer treatment. In view of the safety problems presented by silicone, the search for a safe replacement material has become important.

SUMMARY OF THE INVENTION

It is therefore an object of the invention to provide a breast implant filled with a completely non-toxic material.

It is a further object of the invention to provide a breast implant which will provide a natural feeling breast over a long term.

It is another object of the invention to provide an implant which can be reduced in size over prior art breast implants, but which retains the same cosmetic effect.

To achieve these and other objects, the invention provides a breast implant comprising a non-permeable polymer sac filled with a sugar syrup, optionally mixed with a saline solution. The sugar syrup is preferably honey, but may also be selected from corn syrup, high fructose corn syrup, molasses and other sugar syrups having the requisite concentration and viscosity. The sugar syrups themselves may have widely varying viscosities, with some honey having a viscosity as much as 5000 cp at body temperature and molasses having a viscosity as little as about 850 cp at body temperature. The viscosities of these materials drops rapidly as they are diluted with saline, but the dilution in any event should not produce a viscosity lower than about 15 cp.

The use of the sugar syrup, particularly honey, provides a psychological advantage, as the user is more accepting of a natural material than a synthetic such as silicone, and anxiety over the implant is reduced.

Moreover, the implants of the invention have a better feel than either the silicone-or saline-filled prior art implants. The rheological properties of the implants of the invention, particularly those filled with the higher viscosity syrups, produce an implant that holds its shape better, without sagging. Because the syrup filled implants hold their shape better, their size may be reduced, with a 100 ml honey implant replacing a silicone filled implant of as much as 500 ml. This smaller implant interferes less with mammography.

DETAILED DESCRIPTION OF THE INVENTION

Honey is defined as the nectar and sweet deposits from plants, as gathered, modified and stored in the honeycomb by honeybees. As honey is a natural product, the composition, as well as viscosity, is highly variable, but the major components are fructose, glucose and water. The general composition is set forth below in Table 1:

TABLE 1

|  | Average | Range |
|---|---|---|
| Fructose/Glucose Ratio | 1.23 | 0.76–1.86 |
| Fructose, % wt. | 30.38 | 30.91–44.26 |
| Glucose, % wt. | 30.31 | 22.89–40.75 |
| Minerals (Ash), % wt. | 0.169 | 0.020–1.028 |
| Water, % wt. | 17.2 | 13.4–22.9 |
| Reducing Sugars, % wt. | 76.75 | 61.39–83.72 |
| Sucrose, % wt. | 1.31 | 0.25–7.57 |
| Total Acidity, meg/kg. | 29.12 | 8.68–59.49 |
| True Protein, mg/g. | 168.6 | 57.7–567 |

In addition to the above components, honey also contains small amounts of enzymes, in particular invertase, which converts sucrose into glucose and fructose, amylase and glucose oxidase, which produces gluconic acid and hydrogen peroxide from glucose. Catalase and acid phosphatase may also be present. It is thought that presence of these enzymes may reduce or prevent capsule formation in event of leakage or transmigration.

In addition to honey, other sugar syrups may also be used, particularly corn syrups. Corn syrups are concentrated solutions of partially hydrolyzed starch containing dextrose, maltose and higher molecular weight saccharide. Corn syrups may be classified on their fructose content, with high fructose corn syrup containing about 42 to about 60 wt % fructose.

It is also possible to use molasses, a by-product of the sugar industry which is the mother liquor remaining after crystallization and removal of sucrose from the juices of sugar cane or sugar beet. Molasses composition depends on a number of factors, with cane molasses generally containing about 30 to 40 wt % sucrose and 15 to 20 wt % reducing sugars, and beet molasses containing about 50 to 60 wt % sucrose, a trace of reducing sugars and 0.5 to 2 wt % raffinose.

In addition to the aforementioned naturally occurring sugar syrups, it is possible to formulate a filling material according to the invention by synthetically preparing sugar containing syrup compositions to imitate the properties of a naturally occurring composition. Thus, it is possible to prepare a synthetic honey containing glucose, fructose and sucrose, but without components which could possibly cause allergic reactions.

The sugar syrups of the invention may be used without dilution, or may be diluted up to 50 wt % with physiological saline (aqueous 0.9 wt % NaCl). At the 50% dilution level, the most viscous honey was reduced to a viscosity of about 15 cp, which is the effective minimum for use in the breast implant of the invention. Below a viscosity of about 15 cp, it would be expected that the implant would suffer from the same deflation and wrinkling as the saline solution itself. Viscosities of the various materials in concentrated and diluted form are set forth in Table 2 below. These viscosities were measured at 98.6° F. with a Brookfield viscometer operating with a #27 spindle:

TABLE 2

| Test Fluid | Viscosity (cp) | RPM |
|---|---|---|
| 1. Karo Syrup | 1025 | 50 |
| 2. Grandma's Molasses | 850 | 50 |
| 3. Sue Bee Clove Honey | 1550 | 50 |
| 4. Superior Honey Bear | 4750 | 20 |
| 5. Superior Orange Blossom | 2650 | 50 |
| 6. Silicone | * |  |
| 7. Honey Bear 90%/10% Saline | 650 | 50 |
| 8. Honey Bear 80%/20% Saline | 125 | 50 |
| 9. Honey Bear 95%/5% Saline | 2100 | 50 |
| 10. Honey Bear 70%/30% Saline | 37.5 | 100 |
| 11. Honey Bear 50%/50% Saline | 15 | 100 |

*Too high to measure with available equipment.

The breast implant of the invention will generally be formed with a polymer sac, particularly a silicone sac of the type approved by the FDA. Any other polymer material approved by the FDA for breast implant purposes should also be suitable for the purposes of the present invention.

The specific gravity of honey varies according to the water content, but is generally about 1.4–1.45. Other sugar syrups similarly have a high specific gravity, and weigh considerably more than either water or silicone per unit/volume. For this reason, it is advantageous to use smaller implants. Due to the higher viscosity of the implant material of the invention, smaller implants can be used without the sagging which would be expected from saline implants.

What is claimed is:

1. In a breast implant device comprising a non-permeable polymer sac filled with a filling material, and constructed and arranged for human implantation, the improvement comprising utilizing as said filling material a substantially silicone-free aqueous sugar solution having a viscosity of at least 15 cp at 98.6° F.

2. The device of claim 1, wherein the filling material is selected from the group consisting of honey, corn syrup, high fructose corn syrup, molasses, and mixtures thereof.

3. The device of claim 1, wherein the sugar solution is diluted with physiological saline solution up to 50% by weight.

4. The device of claim 1, wherein the filling material is an aqueous solution of a sugar selected from the group consisting of fructose, glucose, sucrose and mixtures thereof.

5. The device of claim 1, wherein the filling material has a viscosity of at least about 650 cp at 98.6° F.

6. The device of claim 1, where the filling material has a viscosity of at least about 2100 cp at 98.6° F.

7. The device of claim 1, wherein the sac is made of silicone.

* * * * *